(12) United States Patent
Vangelisti et al.

(10) Patent No.: US 7,232,911 B2
(45) Date of Patent: Jun. 19, 2007

(54) PROCESS FOR THE PREPARATION OF 2-AMINOMETHYLPYRIDINE DERIVATIVE

(75) Inventors: Manuel Vangelisti, Charvieu-Chavagneux (FR); Mehul Amin, Suffolk (GB); Robert Pannell, Suffolk (GB)

(73) Assignee: Bayer Cropscience S.A. (FR)

( * ) Notice: Subject to any disclaimer, the term of this patent is extended or adjusted under 35 U.S.C. 154(b) by 217 days.

(21) Appl. No.: 10/535,776

(22) PCT Filed: Nov. 18, 2003

(86) PCT No.: PCT/EP03/14862

§ 371 (c)(1),
(2), (4) Date: May 20, 2005

(87) PCT Pub. No.: WO2004/065359

PCT Pub. Date: Aug. 5, 2004

(65) Prior Publication Data

US 2006/0100441 A1    May 11, 2006

(51) Int. Cl.
*C07D 211/72* (2006.01)
*C07D 211/82* (2006.01)
*C07D 213/79* (2006.01)

(52) U.S. Cl. .................. 546/294; 546/335; 546/329

(58) Field of Classification Search ................ 546/294, 546/335, 329
See application file for complete search history.

(56) References Cited

FOREIGN PATENT DOCUMENTS

| WO | 9942447 | * | 8/1999 |
|----|---------|---|--------|
| WO | WO 99/42447 | | 8/1999 |

OTHER PUBLICATIONS

Hcaplus 131:170272.*
International Search Report dated Jul. 26, 2004.
L. Lecointe et al. "Diastereoselective synthesis of non-proteinogenic alpha-amino acids", Journal Of Peptide Research, vol. 55, No. 4, 2000, pp. 300-307, XP002241714.

* cited by examiner

*Primary Examiner*—Thomas McKenzie
*Assistant Examiner*—Binta Robinson
(74) *Attorney, Agent, or Firm*—Ostrolenk, Faber, Gerb & Soffen, LLP

(57) ABSTRACT

Process for the preparation of 2-aminomethylpyridine derivative of general formula (I), in which: n represents 0, 1, 2 or 3; X is halogen atom; Y may be the same or different and may be a halogen atom, a halogenoalkyl, a alkoxycarbonyl or a alkylsulphonyl

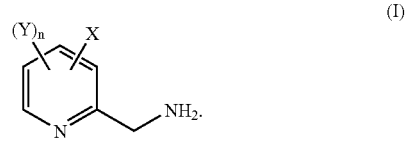

(I)

19 Claims, No Drawings

PROCESS FOR THE PREPARATION OF 2-AMINOMETHYLPYRIDINE DERIVATIVE

CROSS REFERENCE TO RELATED APPLICATIONS

The present application is a 35 U.S.C. §371 national phase conversion of International Application No. PCT/EP2003/014862 filed Nov. 18, 2003, which claims priority of European Patent Application No. 02356235.8 filed Nov. 20, 2002.

The present invention relates to a novel process for the preparation of 2-aminomethylpyridine derivative which is useful as intermediate compound for the preparation of pesticides, starting with benzophenone and glycine alkyl ester hydrochloride.

Patent application WO 99/42447 discloses the preparation of 2-aminomethylpyridines starting from benzophenone glycine imine alkyl ester. This document does not disclose a method for the preparation of benzophenone glycine imine alkyl ester.

Certain methods for the preparation of benzophenone glycine imine alkyl ester have been reported in *Journal of Peptide Research* (2000), 55(4), page 300–307. This article discloses the reaction of benzophenone imine with alkyl glycinate hydrochloride to prepare benzophenone glycine imine alkyl ester. The use of benzophenone is not disclosed in that document. The use of benzophenone imine presents the drawback in that it is expensive. Furthermore, this compound converts into the benzophenone compound during the preparation of 2-aminomethylpyridine compounds thus resulting in an additional step in the process to convert benzophenone into benzophenone imine before recycle, which is undesirable on a commercial plant.

We have now found an alternative method to prepare 2-aminomethylpyridine derivatives which overcomes these problems and which is applicable to industrial scale operation.

Accordingly, the present invention relates to a process for the preparation of a 2-aminomethylpyridine derivative of general formula (I) or a salt thereof:

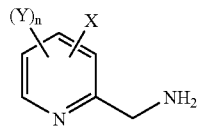
(I)

in which:
n represents 0, 1, 2 or 3,
X is halogen atom,
Y may be the same or different and may a halogen atom, a halogenoalkyl, a alkoxycarbonyl or a alkylsulphonyl;

said process comprising:
(A)—a first step according to reaction scheme 1:

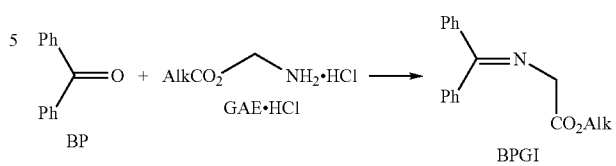

Scheme 1 in which benzophenone (BP) is reacted with glycine alkyl ester hydrochloride (GAE.HCl) at reflux in a non polar solvent, said solvent being capable of forming an azeotrope with water, in the presence of an acid catalyst and a trialkylamine base, in a BP/GAE.HCl molar ratio of from 1 to 4, to provide a benzophenone glycine imine derivative (BPGI);

(B)—a second step according to reaction scheme 2:

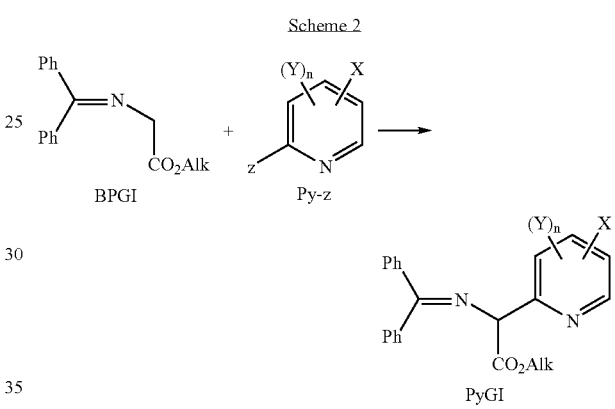

Scheme 2 in which:
X, Y and n are as defined above,
z is a leaving group, comprising the reaction of the benzophenone glycine imine derivative (BPGI) solution obtained in step one with a pyridine derivative (Py-z) in the presence of a dry inorganic base, in the presence of a catalyst and an aprotic polar solvent, the mixture being heated at reflux, to provide a pyridine glycine imine derivative (PyGI);

(C)—a third step according to reaction scheme 3:

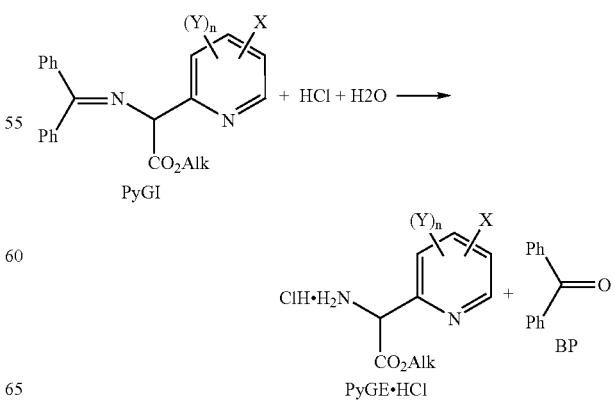

Scheme 3 in which X, Y and n are as defined above comprising the addition to the previous pyridine glycine imine derivative (PyGI) solution of an aqueous hydrochloric acid at a temperature up to 25° C., in a HCl/PyGI molar ratio of at least 1, to provide a pyridine glycine ester hydrochloride derivative (PyGE.HCl);

(D)—a fourth step comprising the conversion of the pyridine glycine ester hydrochloride derivative (PyGE.HCl) into a compound of general formula (I) by heating under reflux of water.

For the purposes of the present invention:

Alk represents a $C_1$–$C_5$ alkyl moiety, preferably ethyl;

haloalkyl means $C_1$–$C_6$ alkyl moiety substituted by one or more halogen atoms;

alkoxycarbonyl means $C_1$–$C_6$ alkoxycarbonyl. Suitable examples of such a moiety may be methoxycarbonyl, ethoxycarbonyl, n-propoxycarbonyl and i-propoxycarbonyl;

alkylsulphonyl means $C_1$–$C_6$ alkysulphonyl;

"Catalyst" means a compound which is used in an amount of 0.01 to 0.2 molar equivalent, preferably from 0.01 to 0.1 molar equivalent of the respective reagent or intermediate compound;

a halogen atom may be a bromine atom, a chlorine atom, a iodine atom or a fluorine atom.

During the preparation of PyGE.HCl from PyGI according to the present invention, benzophenone can be recovered and ready to be directly recycled for benzophenone glycine imine alkyl ester preparation. According to the present invention, benzophenone does not need to be recycled into benzophenone imine, avoiding an expensive additional step. Furthermore, the yield of product obtained by the process according to the present invention is greater than the yield achievable with the processes known from the prior art.

The present invention relates to a process for the preparation of compound of general formula (I). Preferably, the different characteristics of compound of formula (I) may be chosen independently from each other as being:

as regards X, X is chlorine;
as regards n, n is 1;
as regards Y, Y is haloalkyl; more preferably, Y is trifluoromethyl.

More preferably, the present invention relates to a process for the preparation of compound of general formula (I) in which:

X is chlorine;
n is 1;
Y is trifluoromethyl.

The process of the present invention is particularly suitable for the preparation of 2-aminomethyl-3-chloro-5-trifluoromethylpyridine.

The first step (step A) of the process according to the present invention requires the use of a solvent which is capable of forming an azeotrope with water. Suitable solvent includes toluene or ethylbenzene. Step A of the process according to the present invention requires the use of an acid catlayst, preferably paratoluenesulfonic acid catalyst. Step A of the process according to the present invention requires also the use of a trialkylamine base. The preferred trialkylamine base is N,N-diisopropyl N-ethylamine.

The second step (step B) of the process according to the present invention comprises the reaction of the benzophenone glycine imine derivative (BPGI) obtained in step one with a pyridine derivative (Py-z), wherein z is a leaving group, preferably a halogen atom and more preferably a chlorine atom. Step B of the process according to the present invention requires the use of a dry inorganic base. Suitable dry inorganic base includes dry $K_2CO_3$ or NaH. Step B of the process according to the present invention requires the use of a catalyst, preferably a phase transfer catalyst. Suitable phase transfer catalyst may be $NEt_4Br$. Step B of the process according to the present invention also requires the use of an aprotic polar solvent. Suitable solvent may be propionitrile.

The third step (step C) of the process according to the present invention is carried out at a temperature up to 25° C., preferably at a temperature of from 20 to 25° C. Step C is carried out in a HCl/PyGI molar ratio of at least 1, preferably in a HCl/PyGI molar ratio of from 1 to 5.

The product stream obtained in the different steps of the process according to the present invention may be treated to separate and to recycle useful compounds. Such post treatment steps may be carried out according to methods well known by the man ordinary skilled in the art. Particularly, the mixture obtained following to step A may be cooled down and washed with water to dissolve trialkylamine base hydrochloride salt. The two liquid phases may then be separated. The bottom aqueous layer containing the trialkylamine base hydrochloride salt may be separated and treated with aqueous sodium hydroxide to recover trialkylamine base for recycle. The solvent layer which contains the BPGI and the excess of benzophenone may be dried by azeotropic distillation of the solvent and water. The dry solution of BPGI in solvent may then be ready for the coupling reaction with Py-z.

On completion of step B, the aprotic polar solvent is distilled under vacuum for possible recycle. The mixture of PyGI, non polar solvent and excess dry inorganic base may be cooled down at about 20° C. and then washed with water to separate the two phases. A bottom aqueous layer containing excess dry inorganic base may be discarded. The solution of PyGI in non polar solvent and the excess of benzophenone from the previous step may then be ready for the acidification reaction of the step C.

On completion of the step C, two phases may be separated. The bottom aqueous phase containing PyGE.HCl which is ready for the decarboxylation step (step D), and a top non polar solvent phase containing benzophenone. The non polar solvent and benzophenone may be recovered for recycle to the BPGI preparation.

The conversion of PyGE.HCl into compound of general formula (I) according to part D of this process may be performed by known methods such the one described in WO 99/42447 herein incorporated by reference.

During the preparation of PyGE.HCl from PyGI according to the present invention, benzophenone can be recovered for direct recycle into benzophenone glycine imine alkyl ester preparation. According to the present invention, benzophenone does not need to be recycled into benzophenone imine, avoiding an expensive additional step.

Thus, according to another aspect of the present invention there is provided a process for the preparation of pyridine glycine ester hydochloride derivative (PyGE.HCl) according to reaction schemes 1 to 3 as above described.

The present invention will now be illustrated with reference to the following examples.

EXAMPLE 1

Preparation of benzophenone glycine imine ethyl ester

In a 1 litre glass reactor equipped with a distillation section and a Dean and Stark separator, 182 g (1 mole) of benzophenone, 70.1 g (0.5 mole) of glycine ethyl ester hydrochloride, 4.75 g (0.05 mole) of paratoluenesulfonic acid and 249 g of toluene were loaded.

The mixture was heated at 110–115° C. at atmospheric pressure to give a good reflux in toluene. 97 g (1.05 mole) of N,N-diisopropyl N-ethyl amine was added by pump over 4 hours. During the reaction, water was formed and was distilled off as water-toluene azeotrop. Water was decanted in the Dean and Stark separator and toluene was returned to the reactor. Reaction was pursued for 1 hour after the end of the amine addition and completion of the reaction was monitored by liquid chromatography.

When reaction was complete, the reaction mixture was cooled down to 20° C. The mixture was then washed with 335 g of water and the 2 liquid phases were separated by decantation. The bottom aqueous phase containing all N,N-diisopropyl N-ethyl amine hydrochloride was kept for treatment by aqueous sodium hydroxide to recover N,N-diisopropyl N-ethyl amine for recycle.

The upper toluene phase containing benzophenone glycine imine ethyl ester and the excess benzophenone was concentrated during which operation water was removed as an azeotrope with toluene. The dry solution, of benzophenone glycine imine ethyl ester in toluene was assayed by liquid chromatography: a 91% yield of benzophenone glycine imine ethyl ester was obtained with respect to glycine ethyl ester hydrochloride.

EXAMPLE 2

Preparation of ethyl N-(diphenylmethylene)2-(3-chloro-5-trifluoromethyl-2-pyridyl)glycinate In a glass reactor equipped with a distillation section and a Dean and Stark separator, 185 g (3 molar equivalent) of potassium carbonate and 300 g of toluene were loaded. Potassium carbonate was dried of water by refluxing in toluene and distilling off water-toluene azeotrop at a pot temperature of 110° C. 150 g of toluene were removed.

To the dry suspension of potassium carbonate, 4.75 g (0.05 molar equivalent) of tetraethylammonium bromide, 310 g of propionitrile and 380 g (1 molar equivalent of BPGI intermediate) of the previous solution of dry benzophenone glycine imine ethyl ester in toluene were added. The mixture was heated at reflux (105° C.), and 99 g (1 molar equivalent of benzophenone glycine imine ethyl ester intermediate) of 2,3-dichloro-5-trifluoromethyl-pyridine was added by pump over 3 hours, maintaining reflux and separating the condensate in the Dean and Stark condensator, returning solvent to the reaction vessael and discarding water. The reaction completion was monitored by liquid chromatography. Reflux with water removal was continued for a further 3 hours after the end of the pyridine addition. Propionitrile was then distilled off under a reduced pressure of 300 mbar. The reaction mixture was cooled down to 20° C. 315 g of water was added and the 2 liquid phases were separated. The bottom aqueous phase contains all the unreacted potassium carbonate and was discarded. The upper toluene phase of ethyl N-(diphenylmethylene)-2-(3-chloro-5-trifluoromethyl-2-pyridyl)glycinate was assayed by liquid chromatography. A yield of 85% in ethyl N-(diphenylmethylene)-2-(3-chloro-5-trifluoromethyl-2-pyridyl)glycinate with respect to 2,3-dichloro-5-trifluoromethyl-pyridine was obtained.

EXAMPLE 3

Preparation of ethyl 2-(3-chloro-5-trifluoromethyl-2-pyridyl)glycinate

To the ethyl N-(diphenylmethylene)-2-(3-chloro-5-trifluoromethyl-2-pyridyl)glycinate solution in toluene obtained in the previous example, 290 g of aqueous 10% hydrochloric acid were added at 20° C. The reaction was stirred for 1 hour. Conversion of ethyl N-(diphenylmethylene)-2-(3-chloro-5-trifluoromethyl-2-pyridyl)glycinate to ethyl 2-(3-chloro-5-trifluoromethyl-2-pyridyl)glycinate hydrochloride salt was monitored by liquid chromatography for completion.

Two liquid phases were separated. The bottom aqueous phase containing ethyl 2-(3-chloro-5-trifluoromethyl-2-pyridyl)glycinate hydrochloride salt was separated and was ready for the following decarboxylation reaction (preparation of 2-aminomethyl-3-chloro-5-trifluoromethylpyridine hydrochloride). The top organic phase contains all the benzophenone from ethyl N-(diphenylmethylene)-2-(3-chloro-5-trifluoromethyl-2-pyridyl)glycinate and the excess from the BPGI preparation, and was recovered for recycle at step 1. A 93% recovery yield of benzophenone with respect to the 182 g (1 mole) introduced in beinzophenone glycine imine ethyl ester preparation was obtained.

EXAMPLE 4

Preparation of 2-aminomethyl-3-chloro-5-trifluoromethylpyridine hydrochloride

The previous aqueous solution of ethyl 2-(3-chloro-5-trifluoromethyl-2-pyridyl)glycinate was heated under reflux for 7 hours. $CO_2$ formed during the reaction was vented off. After reaction completion, the recovery yield of 2-aminomethylpyridine hydrochloride with respect to PyGI was 86%.

The invention claimed is:

1. Process for the preparation of a 2-aminomethylpyridine derivative of general formula (I) or a salt thereof:

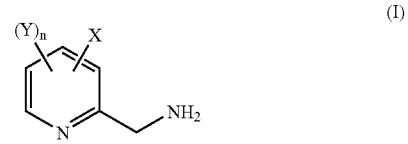

in which:
   n represents 0, 1, 2 or 3,
   X is halogen atom,
   Y may be the same or different and may be a halogen atom, a halogenoalkyl, a alkoxycarbonyl or a alkylsulphonyl;

said process comprising:
   (A)—a first step according to reaction scheme 1:

Scheme 1

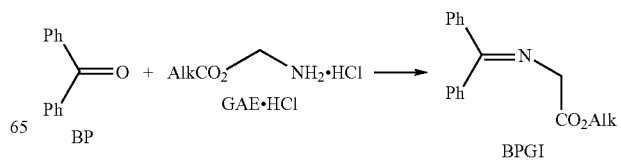

in which benzophenone (BP) is reacted with glycine alkyl ester hydrochloride (GAE.HCl) at reflux in a non polar solvent, said solvent being capable of forming an azeotrope with water, in the presence of an acid catalyst and a trialkylamine base, in a BP/GAE.HCl molar ratio of from 1 to 4, to provide a benzophenone glycine imine derivative (BPGI);

(B)—a second step according to reaction scheme 2;

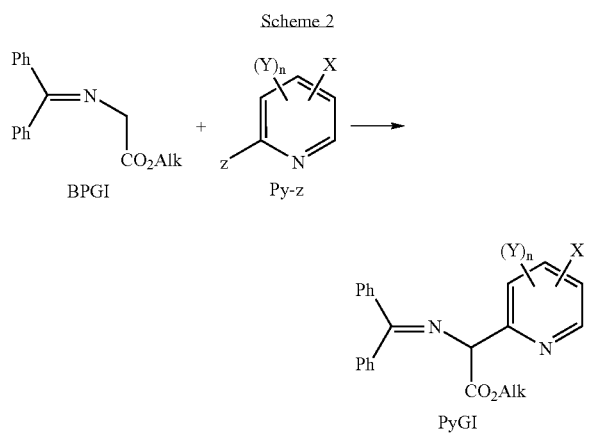

in which:

X, Y and n are as defined above, z is a leaving group, comprising the reaction of the benzophenone glycine imine derivative (BPGI) solution obtained in step one with a pyridine derivative (Py-z) in the presence of a dry inorganic base, in the presence of a catalyst and an aprotic polar solvent, the mixture being heated at reflux, to provide a pyridine glycine imine derivative (PyGI);

(C)—a third step according to reaction scheme 3;

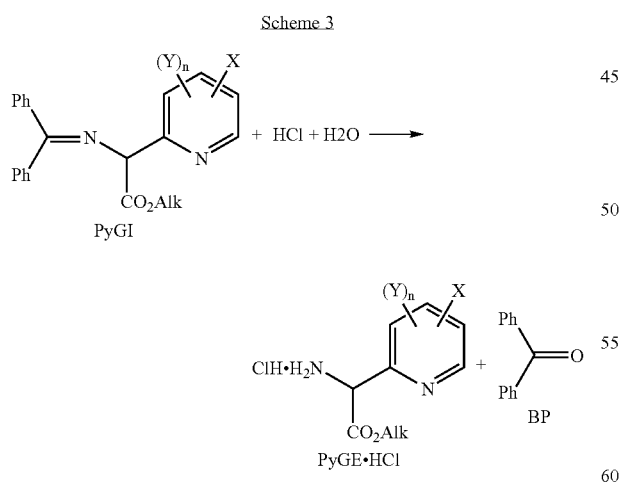

in which X, Y and n are as defined above comprising the addition to the previous pyridine glycine imine derivative (PyGI) solution of an aqueous hydrochloric acid at up to 25° C., in a HCl/PyGI molar ratio of at least 1, to provide a pyridine glycine ester hydrochloride derivative (PyGE.HCl);

(D)—a fourth step comprising the conversion of the pyridine glycine ester hydrochloride derivative (PyGE.HCl) into a compound of general formula (I) by heating under reflux of water.

2. Process according to claim 1, characterised in that X is chlorine.

3. Process according to claim 1, characterised in that n is 1.

4. Process according to claim 1, characterised in that Y is haloalkyl.

5. Process according to claim 4, characterised in that Y is trifluoromethyl.

6. Process according to claim 1, characterised in that X is chlorine, n is 1 and Y is trifluoromethyl.

7. Process according to claim 6, characterised in that compound of general formula (I) is 2-aminomethyl-3-chloro-5-trifluoromethylpyridine.

8. Process according to claim 1, characterised in that, in the first step, the acid catalyst is paratoluenesulfonic acid catalyst.

9. Process according to claim 1, characterised in that, in the first step, the solvent capable of forming an azeotrope with water is toluene or ethylbenzene.

10. Process according to claim 1, characterised in that the trialkylamine base is N,N-diisopropyl N-ethylamine.

11. Process according to claim 1, characterised in that, in the second step, z is a halogen atom.

12. Process according to claim 11, characterised in that z is a chlorine atom.

13. Process according to claim 1, characterised in that, in the second step, the dry inorganic base is $K_2CO_3$ or NaH.

14. Process according to claim 1, characterised in that, in the second step, the catalyst is a phase transfer catalyst.

15. Process according to claim 14, characterised in that the phase transfer catalyst is $Net_4Br$.

16. Process according to claim 1, characterised in that, in the second step, the polar solvent is propionitrile.

17. Process according to claim 1, characterised in that, in the third step, the temperature is of from 20 to 25° C.

18. Process according to claim 1, characterised in that, in the third step the HCl/PyGI molar ratio is of from 1 to 5.

19. Process for the preparation of

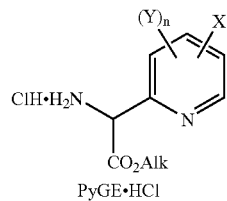

in which:

n represents 0, 1, 2 or 3,

X is halogen atom,

Y may be the same or different and may a halogen atom, a halogenoalkyl, a alkoxycarbonyl or a alkyl-sulphonyl;

said process comprising:

(A)—a first step according to reaction scheme 1;

Scheme 1

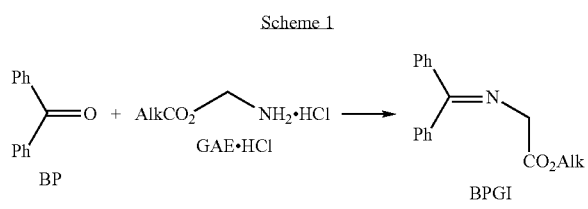

in which benzophenone (BP) is reacted with glycine alkyl ester hydrochloride (GAE.HCl) at reflux in the presence of an acid catalyst and a trialkylamine base, in a non polar solvent, said solvent being capable of forming an azeotrope with water, in a BP/GAE.HCl molar ratio of 1 to 4, to provide a benzophenone glycine imine derivative (BPGI);

(B)—a second step according to reaction scheme 2;

Scheme 2

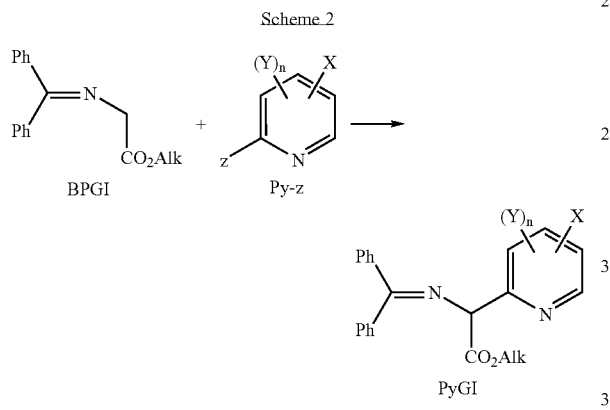

in which:
X, Y and n are as defined above,
z is a leaving group,
comprising the reaction of the benzophenone glycine imine derivative (BPGI) solution obtained in step one with a pyridine derivative (Py-z) in the presence of a dry inorganic base, in which is added a catalyst and an aprotic polar solvent, the mixture being heated at reflux, to provide a pyridine glycine imine derivative (PyGI);

(C)—a third step according to reaction scheme 3;

Scheme 3

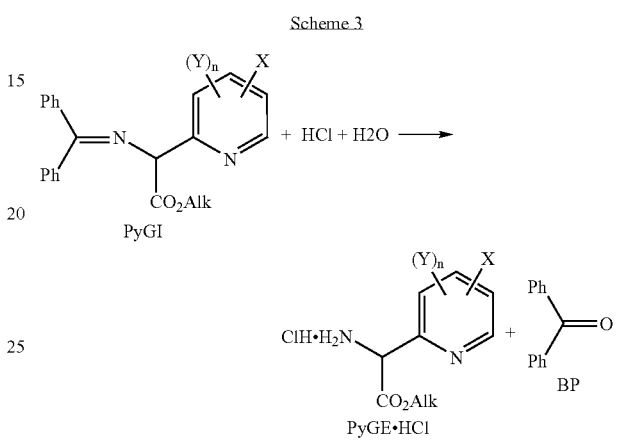

comprising the addition to the previous pyridine glycine imine derivative (PyGI) solution of an aqueous hydrochloric acid at up to 25° C., in a HCl/PyGI molar ratio of at least 1, to provide a pyridine glycine ester hydrochloride derivative (PyGE.HCl).

* * * * *